(12) United States Patent
Alimonti et al.

(10) Patent No.: US 11,235,016 B2
(45) Date of Patent: *Feb. 1, 2022

(54) USE OF A VEGETAL EXTRACT AS AN ACTIVE AGENT IN TISSUE RE-EPITHELIZING AND CICATRIZING PROCESSES

(71) Applicant: Altergon SA, Lugano (CH)

(72) Inventors: Andrea Alimonti, Lugano (CH); Andrea Maria Giori, Lugano (CH); Monica Montopoli, Lugano (CH); Jessica Cadau, Lugano (CH)

(73) Assignee: Altergon SA, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/955,225

(22) PCT Filed: Dec. 14, 2018

(86) PCT No.: PCT/EP2018/085067
§ 371 (c)(1),
(2) Date: Jun. 18, 2020

(87) PCT Pub. No.: WO2019/121425
PCT Pub. Date: Jun. 27, 2019

(65) Prior Publication Data
US 2020/0376064 A1   Dec. 3, 2020

(30) Foreign Application Priority Data
Dec. 19, 2017 (IT) .................. 102017000146620

(51) Int. Cl.
*A61K 36/537* (2006.01)
*A61P 17/02* (2006.01)
*A61K 9/00* (2006.01)
*A61K 38/39* (2006.01)
*A61K 31/722* (2006.01)
(Continued)

(52) U.S. Cl.
CPC .......... *A61K 36/537* (2013.01); *A61K 9/0014* (2013.01); *A61K 31/722* (2013.01);
(Continued)

(58) Field of Classification Search
None
See application file for complete search history.

(56) References Cited

U.S. PATENT DOCUMENTS 3,969,516 A * 7/1976 Stoughton .............. A61K 8/602
514/24

FOREIGN PATENT DOCUMENTS

EP   2762131 A1 *  8/2014  .......... A61K 8/9789
EP   2762131 A1    8/2014

OTHER PUBLICATIONS

Almanza G. et al., "Clerodane diterpenoids and an urbane triterpenoid from Salvia hankie. Computer-assisted structural elucidation", Tetrahedron, vol. 53, No. 43, Oct. 27, 1997, p. 14719-14728.
(Continued)

*Primary Examiner* — Melissa S Mercier
(74) *Attorney, Agent, or Firm* — Silvia Salvadori, P.C.; Silvia Salvadori

(57) ABSTRACT

The use of *Salvia haenkei* extract is described as a re-epithelizing and cicatrizing agent in the treatment of tissue lesions. Pharmaceutical compositions comprising *Salvia haenkei* extract and suitable pharmaceutically acceptable excipients for use in the treatment of tissue lesions are also disclosed.

9 Claims, 1 Drawing Sheet

(51) Int. Cl.
    A61K 33/38    (2006.01)
    A61K 35/02    (2015.01)
    A61K 36/899   (2006.01)
    A61K 38/18    (2006.01)
(52) U.S. Cl.
    CPC .............. *A61K 33/38* (2013.01); *A61K 35/02* (2013.01); *A61K 36/899* (2013.01); *A61K 38/18* (2013.01); *A61K 38/39* (2013.01); *A61P 17/02* (2018.01)

(56) References Cited

OTHER PUBLICATIONS

Evert T. et al., "The relationship between plant use and plant diversity in the bolivian andes, with special reference to medicinal plant use", Human Ecology, vol. 36, No. 6, Dec. 6, 2008, pp. 861-879.
Fournet A. et al., "Leihismanicidal and trypanocidal activities of Bolivian medicinal plants" Journal of Ethnopharmacology, vol. 41, No. 1-2, Jan. 1, 1994, pp. 19-37.
Matic I., et al., "Identification of Salvia hankie as gerosuppressant agent by using an integrated senescence-screening assay", Aging, 2016, vol. 8, No. 12, 3223-3240.
Search report and Written Opinion of PCT/EP2018/085067 dated Apr. 3, 2019.
Topcu G.: "Bioactive triterpenoids from Salvia species", Journal of Natural Poduc, American Chemical Society, US, vol. 69, No. 3, Mar. 9, 2006, pp. 482-487.

* cited by examiner

USE OF A VEGETAL EXTRACT AS AN ACTIVE AGENT IN TISSUE RE-EPITHELIZING AND CICATRIZING PROCESSES

This application is a U.S. national stage of PCT/IB2018/085067 filed on 14 Dec. 2018, which claims priority to and the benefit of Italian Application No. 102017000146620 filed on 19 Dec. 2017, the contents of which are incorporated herein by reference in their entireties.

FIELD OF THE INVENTION

The present invention relates to the use of *Salvia haenkei* extract as a re-epithelizing and cicatrizing agent in the treatment of tissue lesions, being able to offer a significant contribution in tissue regeneration. Furthermore, the present invention also relates to a pharmaceutical composition comprising *Salvia haenkei* extract and suitable pharmaceutically acceptable excipients, for use in the treatment of tissue lesions.

BACKGROUND ART

In all living organisms, from invertebrates to the higher ones, the fundamental response to the loss or damage of a tissue is the restoration of tissue integrity. It is important to clarify the relationship between injury, repair, regeneration. A wound involves structural damage with loss of tissue; it is commonly referred to the local destruction of the skin. Similarly, cicatrization can be defined as the restoration of any part of the body even if the term is commonly used in relation to the body surface. Indeed, cicatrization is both a prerequisite for the regeneration of other tissues, and an actual and true regeneration, in which the re-growth of the coating epithelium and the underlying connective tissue is obtained.

The cicatrization of a wound involves several events: the regeneration of the destroyed tissue, for example the reconstitution of the epithelium, the regeneration of damaged connective tissue, the replacement of dead cells with fibrous tissue.

The abrupt application of a mechanical force on a circumscribed part of the body constitutes a trauma. The traumas can lead to continuous solutions of the lining tissues, with possible injury of the underlying ones, or they can determine the lesions prevalent in the internal organs.

The wound repair process takes place with an almost constant mechanism. It varies somewhat depending on the tissues and general conditions of the organism, but it occurs substantially in two ways: the regeneration of damaged cells with complete restitutio ad integrum, or the formation of a scar that partially replaces the damaged tissues. The first modality is also called repair by first intention, the second repair by second intention or cicatrization. The cells, molecules and mechanisms involved are similar in both conditions; however, in the formation of the scar the reparative process must cope with the replacement of a greater number of cells and, in this, fibroblasts and the production of extracellular matrix are favored.

The wound repair process takes place in various stages, namely: 1) coagulation formation; 2) invasion of the area by phagocytes; 3) proliferation of connective tissues; 4) re-epithelization; 5) remodeling of the area with scar formation. During periods of wound repair, hyaluronic acid, a highly osmotic hygroscopic molecule, allows the control of hydration, stimulating cell infiltration and acting as a promoter in the early stages of the inflammatory process.

The first stage immediately follows the production of the wound. The blood coming out of the vessels begins to coagulate, while the musculature contracts; when the wound is coagulated, the wound bottom will be occupied by a thick network of fibrin. Fibers of fibrin represent safe guides for the subsequent proliferation of fibroblasts. The reconstitution of the tissue takes place according to the orientation of these fibers that favor the contraction of the wound. In this phase, there is also an increase in the content of hyaluronic acid (HA) which forms a matrix to which the cells migrate from the surrounding tissues.

The second phase of the reparative process is characterized by the invasion of the area by phagocytes, i.e. mainly macrophages able to incorporate red blood cells, tissue debris and fibrin.

The third phase of the reparative process consists in the beginning of the proliferation of the connective cells: this affects almost simultaneously both fibroblasts and vascular sketches and is stimulated by growth factors of tissue origin, mostly of peptide nature, which promote the proliferation of fibroblasts (fibroblast growth factor or FGF) and endothelial cells (vascular endothelial growth factor or VEGF). On the morphological plane, the invasion of the coagulum fibroblasts begins around the 2nd-3rd day. As soon as they reach the coagulum, fibroblasts, whose protoplasm is methacromatic with toluidine blue, begin to surround themselves with a halo of extracellular metachromatic substance.

The phenomenon is a prelude to the reconstruction of the fundamental substance, which is precisely processed by these cells. At first, metacromasia seems to be mainly due to hyaluronic acid, then other polysaccharides and proteins appear. At this stage, the microscopic examination of the wound shows a strongly granular red surface, the granules are represented by newly formed capillaries, suggesting a favorable trend in the repair process. The wound in this stage is referred to as "granulating". Along with the morphological changes, biochemical processes proceed in the repair tissue; in particular the content of polysaccharides, first of all the hyaluronic acid, begins to increase, reaching the maximum peak between the second and third days.

The fourth phase of the repair process is the reconstitution of the epithelial lining. This phase, particularly important in the case of superficial wounds, overlaps with the previous ones, but actually begins immediately after the wound has been made. The first event concerning the epithelium is its retraction from the margins of the continuous solution, followed by the sliding towards the center of the wound of the cells of the deeper layers of the epidermis and, mainly, by the thorny layer.

The fifth phase of the repair process is the conclusive one. It is characterized by the progressive increase in the insoluble fraction of collagen and by the gradual replacement of hyaluronic acid with chondroitinsulphuric polysaccharides. The collagen fibers increase in thickness and in number, while the fibroblasts are transformed into fibrocytes. The total number of cells is progressively decreasing and the same happens for the capillaries. The tissue becomes increasingly ischemic. In the final stages of cicatrization, the connective is strongly ialinized and eosinophilic, with no trace of metacromasy, with bundles of elastic fibers intertwined with one another.

From what has been described, it is clear that in human beings the process of tissue repair and regeneration is fundamental to restore the functionality of any tissue subjected to a lesion.

The object of the present invention is therefore to find an effective remedy for the promotion of this process, which is also well tolerated by the organism and which can also be used in cases in which tissue repair, due to intrinsic or external factors, is delayed or compromised, such as in pressure sores, in the diabetic patient and in the elderly patient.

SUMMARY OF THE INVENTION

Said object has been achieved by the use of *Salvia haenkei* extract as a re-epithelizing and cicatrizing agent in the treatment of tissue lesions, as reported in claim 1.

In another aspect, the present invention relates to a pharmaceutical composition comprising *Salvia haenkei* extract and suitable pharmaceutically acceptable excipients, for use in the treatment of tissue lesions.

For the purposes of the present invention, said tissue lesions are maculae, papulae, vesicles, bullae, pustulae, cysts, erosions, abrasions, rashes, ulcers, chapping, sores, decubitus ulcers, telangiectasias, scales, erythema, crusts, lichenifications, excoriations, indurations, cuts, lacerations, diabetic lesions and ulcers, or burns, said lesions occurring to tissues both external, such as the skin, and internal, such as mucous membranes and gingival tissue.

In another aspect, the present invention relates to a pharmaceutical composition comprising *Salvia haenkei* extract and at least one of collagen type II, silver and its derivatives, such as silver sulfadiazine, chondroitin, chondroitin sulfate, dermatan sulfate, keratan sulphate, heparin, heparan sulfate, antibiotics, propolis, amino acids, growth factors, chitosan, chitin, silicates, zeolites, *Triticum vulgare* extract, enzymes such as collagenase, protease and catalase, and mixtures thereof.

BRIEF DESCRIPTION OF THE FIGURES

The characteristics and the advantages of the present invention will become clear from the following detailed description, the working examples provided for illustrative purposes and the accompanying figures, wherein.

DETAILED DESCRIPTION OF THE INVENTION

Figure 1:
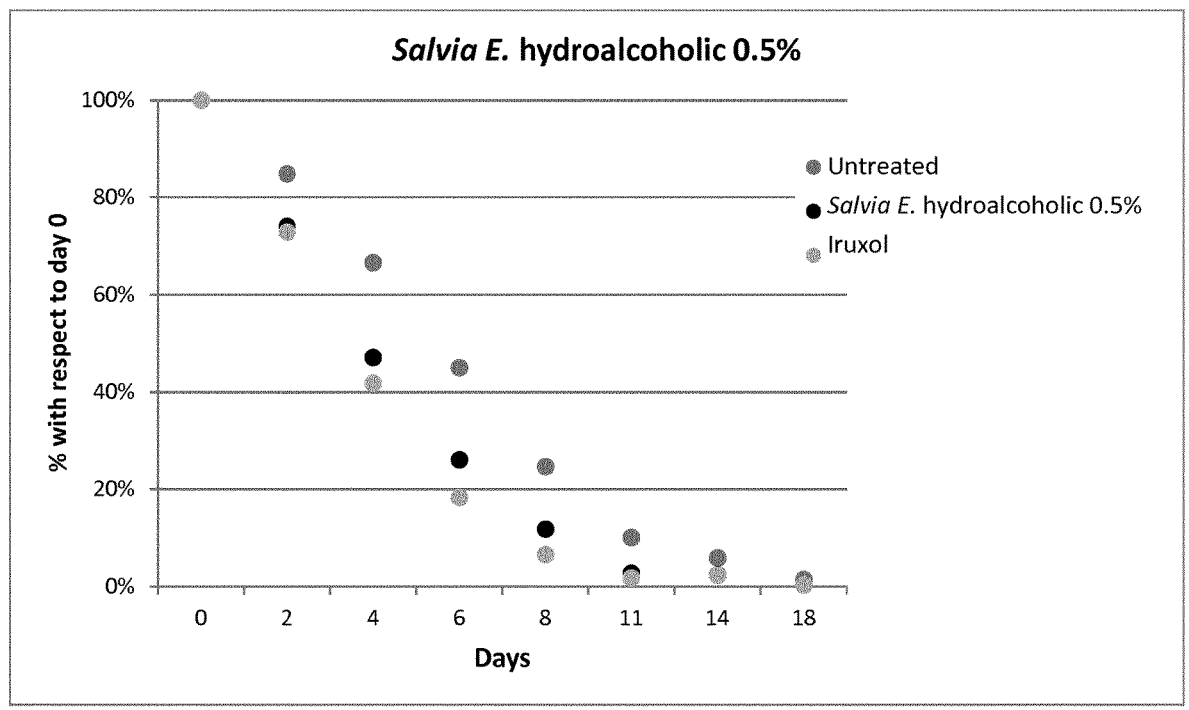
FIG. 1 shows the trend of reclosing the injured area of the treatment group in comparison to the positive (Iruxol®) and negative (untreated) controls, as per Example 2.

*Salvia haenkei* is a shrub coming from Bolivia and Peru, and although it is commonly called "prawn sage" due to the color and shape of its shrimp-like flowers, its scientific name dates from the era of Spanish exploration of the Americas at the end of the eighteenth century. Morphologically, it is characterized by lance-shaped leaves with dentate margins whose length exceeds 12 cm. Their color is light green and the surface is wrinkled. The inflorescence is very long, over 20 cm and is defined as "raceme", i.e. the flowers are inserted at the level of the central axis through the peduncles of the same length at different heights along the same flower axis.

For the preparation of the extract, the aerial parts of the plant are generally used, i.e. stem, leaves, flowers or mixtures thereof. These parts can be used fresh or after drying under controlled conditions. In both cases, the individual parts or mixtures thereof are contacted with a suitable extraction solvent, by using conventional extraction methods, such as maceration or percolation, or more complex techniques, such as for example extraction with ultrasound, microwaves, pressure or supercritical fluids.

After separation of the exhausted plant, the extract can be used as such, or after substitution of the extractive solvent with one more suitable for human use (such as glycerine or glycol, if not used in the extraction phase). Preferably, the extracting solvent is removed to give a dry extract. For the removal of the extractive solvent, the preferred techniques are evaporation at reduced pressure and low temperature, and atomization. The extract can also be subjected to subsequent purification steps, to remove potential contaminants (such as lipophilic pesticides), impurities (such as chlorophyll) or to increase the concentration of secondary metabolites.

The dry extract can be added with suitable excipients, for example to make it smoother, less hygroscopic or standardized in the content of secondary metabolites. Among the excipients that can be used are, for example, silica, maltodextrins, microcrystalline cellulose.

Among the solvents suitable for the preparation of *Salvia haenkei* extract, those with a medium polarity are preferably selected, as being capable of effectively extracting the secondary metabolites of the plant. Preferably, such extraction solvents have dielectric constant of 8 to 60. The so obtained *Salvia haenkei* extract contains a pool of terpenoid compounds, in particular diterpenoids and triterpenoids (Almanza, G. et al., (1997) Clerodane diterpenoids and an ursane triterpenoid from *Salvia haenkei* Computer-assisted structural elucidation, Tetrahedron, 53 (43), pp. 14719-14728), as well as gallic acid and its derivatives, and chlorogenic acid and its derivatives. Some of these compounds are specific to this species of *Salvia* and differentiate it from other species of the same genus, contributing reasonably to the characteristic activity of its extracts.

Examples of usable extraction solvents are alcohols having up to 4 carbon atoms, including diols and triols, aldehydes, ketones, organic esters, chlorinated compounds, and mixtures thereof. When miscible, such solvents can also be used in mixture with water. Preferred solvents include methanol, ethanol, isopropanol, butanol, ethylene glycol, propylene glycol, glycerol, acetone, ethyl acetate and mixtures thereof, as such or mixed with water.

In preferred embodiments, said extraction solvent is a water-alcohol solution, even more preferably it is a 40-80% alcohol solution. Said alcohol is preferably methanol or ethanol. Embodiments in which the extraction solvent is a 60-80% ethanol solution are particularly preferred.

Preferably, the preparation of said *Salvia haenkei* extract comprises the steps of:
1. collecting aerial parts of *Salvia haenkei*,
2. extracting with a solvent,
3. separating the plant exhausted from the liquid extract, and
4. removing the solvent to give the dry extract.

The aerial parts of step 1. may be fresh or preliminarily dried. If the aerial parts are fresh, just harvested, the greater amount of water physiologically present in the plant shall be taken into account.

The invention therefore relates to the use of *Salvia haenkei* extract as a re-epithelizing and cicatrizing agent in the treatment of tissue lesions.

Tissue lesions are are maculae, papulae, vesicles, bullae, pustulae, cysts, erosions, abrasions, rashes, ulcers, chapping, sores, decubitus ulcers, telangiectasias, scales, erythema, crusts, lichenifications, excoriations, indurations, cuts, lacerations, diabetic lesions and ulcers, or burns, said lesions occurring to tissues both external, such as the skin, and internal, such as mucous membranes and gingival tissue.

As will also be seen from the examples provided below, the *Salvia haenkei* extract has shown an unexpected and surprising re-epithelializing and cicatrizing effect on tissue lesions of various kinds, determined by the particular property of modulating the development of connective tissue through a targeted action on collagen and on the fundamental substance. This peculiar action results into a significant improvement in cicatrization, in an improved re-epithelization and in a normalization of the repairing processes towards an altered permeability of the blood vessels.

Preferably, said extract is to be administered via topical route, more preferably via external topical, sub-cutaneous topical, mucosal topical, gingival topical, intravesical topical, vaginal topical, rectal topical, or ocular topical route.

Preferably, said extract is to be administered in a dose of 0.1-1500 mg per day.

In preferred embodiments, said extract is to be administered via external topical route in a dose of 1-1000 mg per day, the effective dosage being a function of the extent and severity of the tissue lesion to be treated.

In another aspect, the present invention relates to a pharmaceutical composition comprising *Salvia haenkei* extract and pharmaceutically acceptable carriers, for use in the treatment of tissue lesions.

Said pharmaceutical composition can be administered via topical route.

Preferably, said pharmaceutical composition is to be administered via external topical, sub-cutaneous topical, mucosal topical, gingival topical, intravesical topical, vaginal topical, rectal topical, or ocular topical route.

In preferred embodiments, said composition is to be administered via external topical route.

Preferably, the pharmaceutical composition comprises *Salvia haenkei* extract in a concentration of 0.1-500 mg/ml of composition, more preferably 1-100 mg/ml.

Said pharmaceutical composition may be in the form of ointment, lotion, cream, emulsion, paste, gel, aqueous solution, spray, patch, serum, soaked gauze, dressing, or a combination thereof.

Said pharmaceutically acceptable vehicles can be rheological additives, buffering agents, antimicrobial agents, antioxidant agents, anti-isothermal agents, antistatic agents, absorbent agents, UV absorbing agents, astringent agents, chelating agents, skin conditioning agents, preservative agents, covering agents, denaturing agents, depigmenting agents, emulsifying agents, film-forming agents, gelling agents, moisturizing agents, hydrotropic agents, binders, soothing agents, smoothing agents, opacifying agents, plasticizing agents, propelling agents, skin protecting agents, reducing agents, cooling agents, sebum-restoring agents, solvents, stabilizing agents, emulsifying stabilizing agents, toning agents, wetting agents, volumizing agents or combinations thereof.

In some embodiments, the pharmaceutical composition for use in the treatment of tissue lesions further comprises at least one other active ingredient, such as collagen type II, silver and its derivatives, such as silver sulfadiazine, glycosaminoglycans, antibiotics, propolis, amino acids, growth factors, chitosan, chitin, silicates, zeolites, or mixture thereof.

Suitable silver derivatives are silver lactate, silver phosphate, silver citrate, silver acetate, silver benzoate, silver chloride, silver carbonate, silver iodide, silver iodate, silver nitrate, silver laurate, silver sulfadiazine, silver palmitate, silver proteinate, or combinations thereof.

Suitable glycosaminoglycans are chondroitin, chondroitin sulphate, dermatan sulfate, keratan sulphate, heparin, heparan sulfate, hyaluronic acid, and mixtures thereof.

In another aspect, the present invention relates to a pharmaceutical composition comprising *Salvia haenkei* extract and at least one of collagen type II, silver and its derivatives, such as silver sulfadiazine, chondroitin, chondroitin sulphate, dermatan sulfate, keratan sulphate, heparin, eparan sulfate, antibiotics, propolis, amino acids, growth factors, chitosan, chitin, silicates, zeolites, *Triticum vulgare* extract, enzymes such as collagenase, protease and catalase, and mixtures thereof.

All the pharmaceutical compositions described above can be prepared by methods known in the pharmaceutical technique.

It should be understood that all the aspects identified as preferred and advantageous for the *Salvia haenkei* extract are to be deemed as similarly preferred and advantageous also for the pharmaceutical compositions and uses thereof.

It should be also understood that all the combinations of preferred aspects of the *Salvia haenkei* extract of the invention, as well as of the pharmaceutical compositions and uses of the same, as above reported, are to be deemed as hereby disclosed.

Below are working examples of the present invention provided for illustrative purposes.

EXAMPLES

Example 1

Preparation of *Salvia haenkei* Extracts 10 kg of aerial parts of *Salvia haenkei* are harvested from field crops, which are then subjected to a drying process in a ventilated dryer under controlled conditions.

In this way, 1.95 kg of dried plant are obtained, which are minced into a bladed mill to give dried and ground *Salvia haenkei*.

This is used as raw material for the subsequent solvent extraction tests carried out as described below:

1. 100 g of dried and ground *Salvia haenkei* are introduced into a static percolator and covered completely with 200 ml of a water and ethanol 30-70% v/v mixture. It is left to stand for 2 hours and the extraction solvent (170 ml) is recovered from the bottom of the percolator, which is set aside (extract 1);
2. the humid plant left in the percolator is covered with a new 70% aqueous ethanol (170 ml) aliquot, leaving it to rest for 2 hours. The solvent is recovered (165 ml-extract 2);
3. the extraction described in point 2 is repeated until the dry residue of the extract recovered is less than 5% of the total dry residue extracted up to that moment. At that point, the extraction is considered completed and the spent moist plant is eliminated. 6 extractions are required;
4. the extracts obtained from the individual extraction steps (from extract 1 to extract 6) are combined, filtered and concentrated in a rotary evaporator under vacuum, at a low temperature. It is proceeded until a concentrated, viscous solution (35 ml) is obtained;
5. the concentrated extract is transferred to a steel tray and inserted into a under vacuum cabinet dryer, with heating set at 30° C. After 12 hours, the solvent is completely removed (extract weight loss less than 10%, i.e.

dry residue higher than 90%). 14.3 g of integral dry extract are obtained. The ratio drug:extract (DER) is 7:1 (extract 1A).
6. the dried extract obtained is added with 10 g of maltodextrin (DE 10) to improve its consistency and the mixture is milled and sieved, thus obtaining 23.7 g of ground dry extract.

By applying the same procedure but different extracting solvents different native dry extracts were prepared.

The table summarizes the results of the various extraction tests:

| extract | extraction solvent | DER |
|---------|-------------------|------|
| 1A | ethanol:water 70:30 | 7:1 |
| 1B | ethanol:water 95:5 | 9.5:1 |
| 1C | acetone | 11:1 |
| 1D | methanol | 8:1 |
| 1E | ethyl acetate | 15:1 |
| 1F | water | 5:1 |
| 1G | methanol:water 50:50 | 6:1 |

Example 2

The aim of this study was the evaluation of the bioactivity of the hydroalcoholic extract of *Salvia haenkei* of Example 1A, to verify its re-epithelizing and cicatrizing power. To do this, tissue damage was induced by an excisional model in mice.

In particular, the model was established in mice of the BALB/c strain of 6-7 weeks. The animals were divided into experimental groups: a positive control group (treated with a healing cream, Iruxol®, i.e. 1% collagenase+60 IU chloramphenicol), a negative (untreated) control group, and a group treated with the hydroalcoholic *Salvia haenkei* extract (briefly "*salvia* A" at 0.5%, or 5 mg/ml). The tested formulations, with the same formulation of the excipients, were topically administered every day for a period of 18 days, covering the wound with a quantity of product to cover an area equal to 19.6 mm².

Said excipients were:
10% Glycerol
7% Sorbitol 70%
1% Carbomer
0.3% Sodium hydroxide
balance to 100% purified water The wound closure was monitored and documented by taking photographs on alternate days. The acquired images allowed to make measurements by using dedicated software in order to quantify the bioactivity of the tested products.

The data obtained confirmed the active role of *salvia* A in wound repair processes.

Results

The cicatrizing potential of the tested formulations is expressed in terms of wound closure, i.e. the percentage ratio between the area healed and the total area of the lesion in question, normalized taking into account the absolute measurement error.

Figure 2:
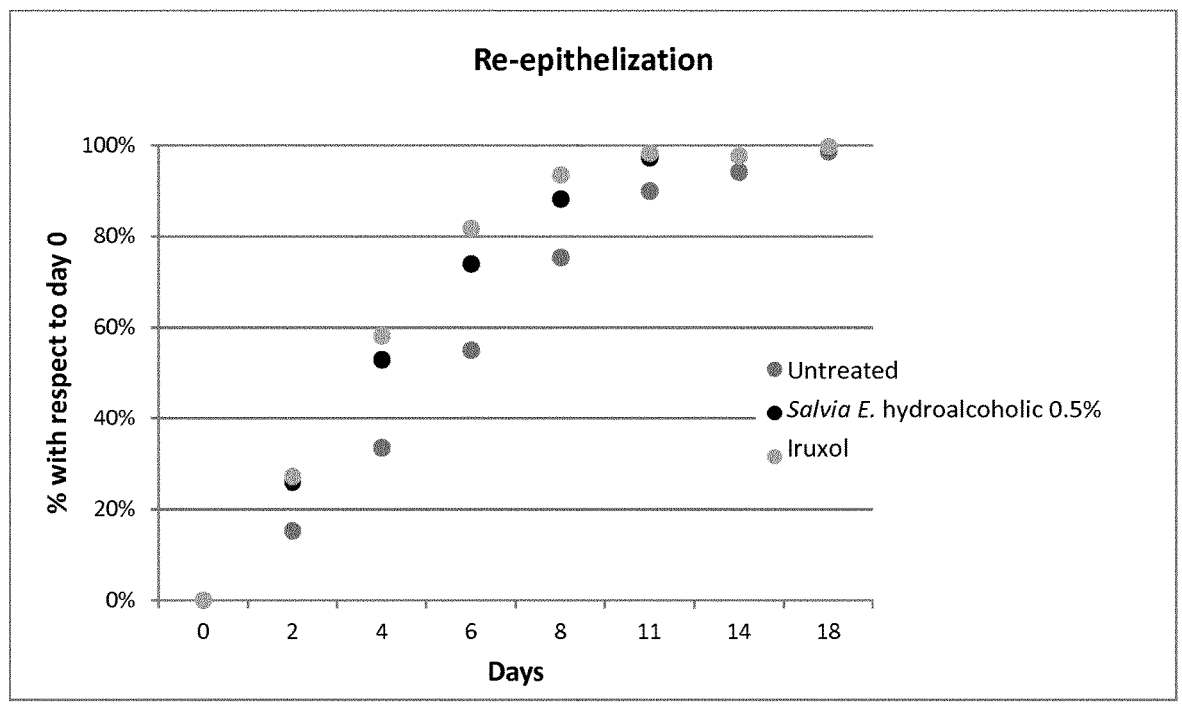
FIG. 2 shows the trend in % (calculated on the group mean) of tissue re-epithelialization of the treatment group compared to the positive (Iruxol®) and negative (untreated) controls, as per Example 2.

With reference to FIGS. 1 and 2, the trend of the "front" of re-epithelialization on day 2 showed similarities in the two groups treated, respectively, with *Salvia* A 0.5% and Iruxol® (positive control), for which a greater "closure" of the epithelial borders. Treatment with the reference compound used as a positive control induced a significant reduction of the injured area compared to the untreated group, starting from the fourth day of treatment and for the entire duration of the study, leading to a statistical forecast of the closure of the 50% in only 2 days and complete re-epithelization about 2.5 days before the untreated group (13.5 vs. 15.9 days).

A behavior similar to that of the positive control was observed for the treatment with *Salvia* A. *Salvia* A, in fact, induced a re-epithelization of the injured area, between day 4 and day 11, significantly greater than that observed for the untreated group. Furthermore, the trend of the re-epithelization of the injured area of the group with *Salvia* A was comparable to that of the group treated with Iruxol.

The treatment with *Salvia* A, moreover, led to a re-epithelization equal to 50% of the initial injured area already after 2.7 days and to complete re-closure after 14.2 days (statistical forecast), almost 2 days before the untreated group.

In conclusion, the data obtained at 3 weeks of treatment showed that the hydroalcoholic extract of *Salvia haenkei* at the concentration of 0.5% has a cicatrizing effect equal to that of the control drug.

The data obtained in this study lead to consider positive the use of the hydroalcoholic extract of *Salvia haenkei* in the days following the induction of the damage. The use of the hydroalcoholic extract of *Salvia haenkei* 0.5% in re-epithelialization of epithelial tissues has proven to be effective since the second day of application and in determining a better and faster wound cicatrization, which is close to completion after 11 days of treatment, like positive control. In fact, the results on the re-epithelialization times are excellent and superimposable to those obtained with the treatment with the control drug Iruxol®, both in the early and in the late stages of healing. *Salvia* A has proven to be effective in reducing post-excisional bleeding, already on the first or second day of application, thus decreasing the discomfort present following the application of the splitting membrane and therefore showing itself useful in reducing the clinical signs of tissue inflammation. The product has therefore shown a good bioactivity in terms of anti-inflammatory and anti-hemorrhagic properties in the tissues.

It can therefore be stated that the hydroalcoholic extract of *Salvia haenkei* can give good results as a cicatrizing and re-epithelializing agent.

The invention claimed is:

1. A method of re-epithelizing and cicatrizing tissue lesions, said method comprising
   administering to a subject in need thereof a *Salvia haenkei* extract as a re-epithelizing and cicatrizing agent, and re-epithelizing and cicatrizing said tissue lesions,
   wherein said tissue lesions are maculae, papulae, vesicles, bullae, pustulae, cysts, erosions, abrasions, rashes, ulcers, chapping, sores, decubitus ulcers, telangiectasias, scales, erythema, crusts, lichenifications, excoriations, indurations, cuts, lacerations, diabetic lesions and ulcers, or burns.

2. The method of claim 1, wherein said extract is to be administered via external topical route.

3. The method of claim 1, wherein said extract is to be administered via external topical route in a dose of 1-1,000 mg per day.

4. The method of claim 1, wherein the *Salvia haenkei* extract is in the form of a pharmaceutical composition further comprising pharmaceutically acceptable vehicles.

5. The method of claim 4, said pharmaceutical composition being administered via external topical route.

6. The method of claim 5, said composition being in the form of ointment, lotion, cream, emulsion, paste, gel, aqueous solution, spray, patch, serum, soaked gauze, dressing, or a combination thereof.

7. The method of claim 4, said pharmaceutical composition comprising *Salvia haenkei* extract in a concentration of 0.1-500 mg/ml of said pharmaceutical composition.

8. The method of claim 4, said pharmaceutical composition further comprising collagen type II, silver and its derivatives, glycosaminoglycans, antibiotics, propolis, amino acids, growth factors, chitosan, chitin, silicates, zeolites, *Triticum vulgare* extract, enzymes selected from the group consisting of collagenase, protease and catalase, and mixtures thereof.

9. A pharmaceutical composition comprising *Salvia haenkei* extract and at least one of collagen type II, silver and its derivatives, consisting from the group consisting of silver sulfadiazine, chondroitin, chondroitin sulfate, dermatan sulfate, keratan sulphate, heparin, heparan sulfate, antibiotics, propolis, amino acids, growth factors, chitosan, chitin, silicates, zeolites, *Triticum vulgare* extract, enzymes such as collagenase, protease and catalase, and mixtures thereof.

* * * * *